US006979547B2

(12) United States Patent
Huang (10) Patent No.: US 6,979,547 B2
(45) Date of Patent: Dec. 27, 2005

(54) METHODS FOR DESIGNING SPECIFIC ION CHANNEL BLOCKERS

(75) Inventor: Xin-Yun Huang, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 481 days.

(21) Appl. No.: 09/273,217

(22) Filed: Mar. 19, 1999

(65) Prior Publication Data

US 2003/0023041 A1 Jan. 30, 2003

Related U.S. Application Data

(60) Provisional application No. 60/079,268, filed on Mar. 25, 1998.

(51) Int. Cl.[7] .................. G01N 33/53; A61K 39/395
(52) U.S. Cl. .................. 435/7.2; 435/7.1; 435/7.21; 424/146.1
(58) Field of Search .................. 435/7.1, 7.2, 7.21, 435/69.1, 320.1; 530/300, 350, 324; 424/146.1

(56) References Cited

U.S. PATENT DOCUMENTS

| | | | |
|---|---|---|---|
| 4,824,529 A | 4/1989 | Thompson et al. ............ 204/1 |
| 4,950,591 A | 8/1990 | Cherksey ...................... 435/7 |
| 4,954,436 A | 9/1990 | Froehner et al. .............. 435/7 |
| 5,208,145 A | 5/1993 | Rogers ......................... 435/6 |
| 5,356,775 A | 10/1994 | Hebert et al. ................. 435/6 |
| 5,380,836 A | 1/1995 | Rogart ...................... 536/23.5 |
| 5,386,025 A | 1/1995 | Jay et al. ................... 536/23.5 |
| 5,401,629 A | 3/1995 | Harpold et al. ............... 536/6 |
| 5,436,170 A | 7/1995 | Cornell et al. ............. 436/527 |
| 5,437,982 A | 8/1995 | Catterall et al. ............ 435/7.2 |
| 5,449,609 A | 9/1995 | Younkin et al. ........... 435/7.21 |
| 5,451,504 A | 9/1995 | Fitzpatrick et al. ........ 435/7.2 |
| 5,827,655 A * | 10/1998 | Chandy et al. ................. 435/6 |
| 6,077,680 A * | 6/2000 | Kem et al. .................. 435/7.24 |

FOREIGN PATENT DOCUMENTS

| | | |
|---|---|---|
| WO | WO 90/10871 A1 | 9/1990 |
| WO | WO 96/10091 A1 | 4/1996 |

OTHER PUBLICATIONS

Stuhmer, W., et al., Molecular basis of function diversity of Voltage–gated potassium channels in mammalian brain, The EMBO journal, vol. 8, No. 11, pp. 3235–4244, 1989.*

Chandy, K.G., et al., A Family of Three Mouse Potassium Channel Genes with Intronless Coding Regions, Science, vol. 247, pp. 973–975, 1990.*

Tejedor, F. et al., Site of covalent attachment of alpha–scorpion toxin derivatives in domain I of sodium channel alpha subunit, Proc. Natl. Acad. Sci. UDA, vol. 85. pp. 8724–8746, 1988.*

Yatani et al., "A Monoclonal Antibody of the $\alpha$ Subunit of $G_K$ Blocks Muscarinic Activation of Atrial $K^+$ Channels," Science 241:828–31 (1988).

Vassilev et al. "Identification of an Intracellular Peptide Segment Involved in Sodium Channel Inactivation," Science 241:1658–61 (1988).

Morton et al., "Monoclonal Antibody to the $\alpha_1$–Subunit of the Dihydropyridine–Binding Complex Inhibit Calcium Current in BC3H1 Myocytes,"*J. Biol. Chem.*, 263(2):613–616 (1988).

Koch et al., "Complex Subunit Assembly to Neuronal Voltage–Gated $K^{31}$ Channels,"*J. Biol Chem.*, 272(44):27577–27581 (1997).

Koschak, et al., "Subunit Composition of Brain Voltage-Gated Potassium Channels Determined by Hongotoxin–1, a Novel Peptide Derived from *Centruroides limbans*Venom," *J. Biol. Chem.*, 273(5):2669–2644.

Zhou, et al., "Specific Antibodies to the External Vestibule of Voltage–Gated Potassium Channels Block Current,"*J. Gen. Physiol.*, 111:555–563 (1998).

* cited by examiner

*Primary Examiner*—Lorraine Spector
*Assistant Examiner*—Zachary C. Howard
(74) *Attorney, Agent, or Firm*—Nixon Peabody LLP

(57) ABSTRACT

The present invention relates to a method of designing an ion channel blocker for an ion channel which includes providing an ion channel having an external vestibule portion and raising an antibody, binding portion, probe, or ligand specific to the external vestibule portion of the ion channel, where the antibody, binding portion, probe, or ligand inhibits ion transport through the ion channel. The present invention further relates to a method of inhibiting ion transport through an ion channel, a method for screening a drug for effectiveness as an ion channel blocker, and an antibody, binding portion, probe, or ligand.

14 Claims, 7 Drawing Sheets

SEQUENCE LISTING

```
<160> NUMBER OF SEQ ID NOS: 4

<210> SEQ ID NO 1
<211> LENGTH: 15
<212> TYPE: PRT
<213> ORGANISM: rat

<400> SEQUENCE: 1

Phe Ala Glu Ala Asp Glu Arg Asp Ser Gln Phe Pro Ser Ile Pro
 1               5                  10                  15

<210> SEQ ID NO 2
<211> LENGTH: 15
<212> TYPE: PRT
<213> ORGANISM: rat

<400> SEQUENCE: 2

Asp Pro Leu Arg Asn Glu Tyr Phe Phe Asp Arg Asn Arg Pro Ser
 1               5                  10                  15

<210> SEQ ID NO 3
<211> LENGTH: 14
<212> TYPE: PRT
<213> ORGANISM: rat

<400> SEQUENCE: 3

Gly Ala Gln Pro Asn Asp Pro Ser Ala Ser Glu His Thr His
 1               5                  10

<210> SEQ ID NO 4
<211> LENGTH: 15
<212> TYPE: PRT
<213> ORGANISM: rat

<400> SEQUENCE: 4

Phe Ala Glu Ala Asp Asp Pro Thr Ser Gly Phe Ser Ser Ile Pro
 1               5                  10                  15
```

METHODS FOR DESIGNING SPECIFIC ION CHANNEL BLOCKERS

This application claims benefit of U.S. Provisional Patent Application Ser. No. 60/079,268, filed Mar, 25, 1998.

BACKGROUND OF THE INVENTION

Cell membranes must allow passage of various polar molecules, including ions, sugars, amino acids, and nucleotides. Special membrane proteins are responsible for transferring such molecules across cell membranes. These proteins, referred to as membrane transport proteins, occur in many forms and in all types of biological membranes. Each protein is specific in that it transports a particular class of molecules (such as ions, sugars, or amino acids) and often only certain molecular species of the class. All membrane transport proteins that have been studied in detail have been found to be multipass transmembrane proteins. By forming a continuous protein pathway across the membrane, these proteins enable the specific molecules to cross the membrane without coming into direct contact with the hydrophobic interior of the lipid bilayer of the plasma membrane.

There are two major classes of membrane transport proteins: carrier proteins and channel proteins. Carrier proteins bind the specific molecule to be transported and undergo a series of conformational changes in order to transfer the bound molecule across the membrane. Channel proteins, on the other hand, need not bind the molecule. Instead, they form hydrophilic pores that extend across the lipid bilayer; when these pores are open, they allow specific molecules (usually inorganic ions of appropriate size and charge) to pass through them and thereby cross the membrane. Transport through channel proteins occurs at a much faster rate than transport mediated by carrier proteins.

Channel proteins which are concerned specifically with inorganic ion transport are referred to as ion channels, and include ion channels for sodium, potassium, calcium, and chloride ions. Ion channels which open in response to a change in the voltage across the membrane are referred to as voltage-sensitive ion channels.

Ion channels serve numerous physiological functions in excitable and nonexcitable cells (Catterall, W. A., *Science* 242: 50–61 (1988); Lester, H. A., *Annu. Rev. Physiol.* 53: 477–496 (1991); Jan. L. Y. et al., *Annu. Rev. Physiol.* 54: 537–555 (1992)). They transmit electrical signals to generate physiological cell responses. With electrophysiological recording techniques, a variety of ionic currents in many kinds of cells have been observed (Catterall, W. A., *Science* 242: 50–61 (1988); Lester, H. A., *Annu. Rev. Physiol.* 53: 477–496 (1991); Jan. L. Y. et al., *Annu. Rev. Physiol.* 54: 537–555 (1992)). The importance of these ionic currents has been demonstrated by pharmacological approaches using either naturally existing ion channel toxins or inorganic and organic ion channel blockers (such as local anesthetics). The essential physiological roles of ion channels in normal cellular functions have been further strengthened by the link of diseases to defects in ion channel genes (Catterall, W. A., *Science* 242: 50–61 (1988); Lester, H. A., *Annu. Rev. Physiol.* 53: 477–496 (1991); Jan. L. Y. et al., *Annu. Rev. Physiol.* 54: 537–555 (1992)).

Over the past few years, molecular biological studies have revealed a large number of ion channel genes that could be responsible for the observed ionic currents (Pongs, O., *Physiol. Rev.* 72:S69–88 (1992); Perney, T. M. et al., *Semin. Neurosci.* 5:135–145 (1993); Chandy, K. G. et al., In CRC *Handbook of Receptors and Channels* ed. North, R. A. (Boca Raton, Fla.: CRC), pp. 1–71 (1995); Deal, K. K. et al., *Physiol. Rev.* 76: 49–67 (1996)). For example, there are more than 20 genes that have been cloned coding for voltage-gated potassium channels (Pongs, O., *Physiol. Rev.* 72:S69–88 (1992); Perney, T. M. et al., *Semin. Neurosci.* 5: 135–145 (1993); Chandy, K. G. et al., In CRC *Handbook of Receptors and Channels* ed. North, R. A. (Boca Raton, Fla.: CRC), pp. 1–71 (1995); Deal, K. K. et al., *Physiol. Rev.* 76:49–67 (1996)). Just within the Kv1 subfamily of the voltage-gated $K^+$ channels, there are at least seven members, and most of them (except Kv1.4) generate similar delayed-rectifier $K^+$ currents. Moreover, different potassium channel subunits can co-assemble to form heteromultimeric channels (Isacoff, E. Y. et al., *Nature* 345:530–534 (1990); Ruppersberg, J. P. et al., *Nature* 345: 535:537 (1990); Christie, M. J. et al., *Neuron* 2:405–411 (1990)). Finally, the native complex of voltage-gated $K^+$ channels is also composed of accessory β-units and these β-subunits could convert the delayed-rectifier currents into rapidly inactivating A-type $K^+$ currents (Rettig, J. et al., *Nature* 369:289–294 (1994)).

Antibodies have previously been used in functional studies of channels. Antipeptide antibodies, made against regions between S5 and S6 transmembrane segments of domains I and IV of the sodium channel α-scorpion toxin to sodium channels reconstituted in phospholipid vesicles or synaptosomes (Thomsen et al., *Proc. Natl. Acad. Sci. USA* 86:10161–10165 (1989)). It was not shown whether these antibodies could block sodium currents. An antipeptide antibody, by binding to a region in the intracellular loop between domains III and IV, slows sodium channel inactivation (Vassilev et al., *Science* 241:1658–1661 (1988)). Furthermore, it has been found that antisera from patients with Lambert-Eaton Myasthenic Syndrome (an autoimmune disease of neuromuscular transmission) could inhibit calcium channel currents (Kim et al., *Science* 239:405–408 (1988)). Antisera from some patients with Isaacs' Syndrome (acquired neuromyotonia) have antibodies against potassium channels and could increase neuronal excitability, possibly due to blocking of potassium currents (Shillito et al., *Ann. Neuol.* 38:714–722 (1995)). One monoclonal antibody that was generated against membrane fragments of the eel electroplax attenuates sodium current (Meiri et al., *Proc. Natl. Acad. Sci. USA* 88:8385–8399 (1986)). Another monoclonal antibody that recognizes the dihydropyridine-binding complex in rabbit muscle transverse tubules inhibits calcium current in a mouse muscle cell line (Morton et al., *J. Biol Chem.* 263:613–616 (1988)). However, in all these cases, the binding sites on the channel proteins was not clear.

The challenge now is to pin-point the underlying molecular identities (ion channel proteins) responsible for the observed ionic currents in native cells and to define their physiological functions. Although genetic manipulation with targeted deletion of ion channel genes would be helpful, the interpretation of results could be complicated by functional redundancy and developmental abnormalities. Some ion channel blockers are available, but they usually affect a group of ion channels and, thus, lack specificity towards one specific channel protein. These blockers were found empirically, either by clinical use or by broad functional screening, rather than by rational design. The present invention is directed to overcoming these deficiencies.

SUMMARY OF THE INVENTION

The present invention relates to a method of designing an ion channel blocker for an ion channel which includes providing an ion channel having an external vestibule portion and providing an antibody, binding portion, probe, or ligand specific to the external vestibule portion of the ion channel, where the antibody, binding portion, probe, or ligand is effective to inhibit ion transport through the ion channel.

Another aspect of the present invention relates to a method of inhibiting the ion transport through an ion channel having an external vestibule portion which includes providing an ion channel blocker which is specific to the external vestibule portion of the ion channel under conditions effective to inhibit ion transport through the ion channel.

Yet another aspect of the present invention relates to a method of screening a drug for effectiveness as an ion channel blocker for an ion channel where the ion channel has an external vestibule portion. The method includes contacting a cell having an ion channel with an ion channel blocker candidate and evaluating the cell to determine if the ion channel blocker candidate binds to the external vestibule portion of the ion channel and inhibits ion transport through the ion channel.

Yet another aspect of the present invention relates to an antibody where the antibody, binding portion, probe, or ligand which inhibits ion transport of an ion channel by binding to an external vestibule portion of the ion channel.

A number of compounds useful in treating various diseases in animals, including humans, are thought to exert their beneficial effects by modulating the functioning of ion channels. An understanding of the pharmacology of compounds that interact with ion channels, and the ability to rationally design compounds that will interact with ion channels to have desired therapeutic effects, have been hampered by the lack of rapid, effective means to identify those compounds which interact with specific ion channels. The availability of rapid, effective means to identify compounds which interact with ion channels would enable the rapid screening of a large number of compounds to identify those candidates suitable for further, in-depth studies of therapeutic applications. With the method of the present invention, blockers for each specific ion channel based on available nucleotide or amino acid sequence information are rationally designed. Using a specific antibody against the external vestibule of a channel protein, the specific blocking of this channel is achieved by this antibody, but other related channels are not blocked. This approach provides a method to rationally design specific ion channel blockers.

DESCRIPTION OF THE FIGURES

In FIG. 1A, the amino acid sequence alignment of rKv1.2, hKv1.3 and rKv3.1 shows the S5 and S6 transmembrane domains, the pore-forming region (P region) and indicates the peptide used for generating the blocking antibody (underlined). Dashes represent same amino acids as rKv1.2. In FIG. 1B, a schematic model is shown for the proposed arrangement of the external vestibule of Kv1.2. The peptide used for generating the blocking antibody is in bold and shaded. Only the flanking S5 and S6 domains and two of the four subunits of the channel are illustrated. FIGS. 1C and 1D are a characterization of Kv1.2-BA and Kv1-NA antibodies. Membrane preparations from HEK-293 cells, untransfected (lanes 1), transfected with Kv1.2 (lanes 2 and 4), or transfected with Kv1.3 (lane 3), were subjected to 10% SDS-polyacrylamide gel electrophoresis and were Western blotted with Kv1.2BA antibody (FIG. 1C) or Kv1-NA antibody (FIG. 1D). Estimated molecular masses of Kv1.2 and Kv1.3 were 70 to 80 kDa. Bands representing endogenous Kv1 proteins could be seen upon longer exposure. FIG. 1E illustrates characterization of the Kv3.1-BA antibody. Membrane preparations from HEK-293 cells, untransfected (lane 1), transfected with Kv3.1 (lanes 2 and 4), or transfected with Kv1.2 (lane 3) were subjected to SDS-PAGE and were Western blotted with Kv3.1-BA antibody. Lane 4 was probed with Kv3.1-BA that had been preincubated with the peptide used to generate Kv3.1-BA. Estimated molecular mass of Kv3.1 was 100 kD. Positions of prestained molecular mass markers in kilodaltons are indicated on the left.

FIG. 2A shows Kv1.2 currents in Kv1.2 stably transfected HEK-293 cells in the absence of Kv1.2-BA (HEK/Kv1.2 cells) or in the presence of Kv1.2-BA (+Kv1.2-BA). Untransfected HEK-293 cells have very small endogenous currents (HEK). Addition of 250 nM Kv1.2-BA resulted in an about 70% suppression of Kv1.2 currents. Whole-cell currents were elicited by voltage pulses of 300-ms duration from a holding potential of −70 mV. Current was measured in the range from −40 mV to 60 mV varying the voltage in 10-mV steps. FIG. 2B shows a time course of the blockage of Kv1.2 currents by Kv1.2-BA (+Kv1.2-BA). In the absence of Kv1.2-BA, the Kv1.2 current is quite stable for over 15 minutes (HEK/Kv1.2). Peak currents (I) at +60 mV at each time point are compared with the currents ($I_a$) before the addition of the antibody. FIG. 2C shows the current-voltage relationship of whole-cell currents. All currents (I) are expressed as a fraction of the peak current ($I_{max}$) at +60 mV in the absence of the antibody. FIG. 2D shows that Kv1.2-BA blockage is concentration-dependent. Data points were taken at 15 minutes after the addition of antibody. The data are mean±standard deviation of five to seven (n) experiments. FIG. 2E shows whole-cell potassium currents from Kv 1.2-transfected HEK-293 cells in the absence of (HEK/Kv1.2) or in the presence (+Kv1.2-BA) of the blocking antibody Kv1.2-BA. Kv1.2-BA (250 nM) reduced the whole cell K+ currents by about 70%. Preincubation of Kv1.2-BA with excess of the immunogenic peptide (Kv1.2-BA+ peptide) reduced the suppression to the residual effect of about 25%. Preincubation of Kv1.2-BA with excess of a control peptide (the Kv1-NA immunogenic peptide) had no effects on Kv1-2-BA suppression of Kv1.2 currents.

FIGS. 3A and 3B show that a control antibody, Kv1-NA (250 nM), has a limited effect on Kv1.2 currents. FIGS. 3C and 3D show that Kv1.2-BA (250 nM) has limited effect on Kv1.3 currents in Kv1.3 stably transfected HEK-293 cells. FIGS. 3E and 3F show that Kv1.2-BA (250 nM) has no significant effect on Kv3.1 currents in Kv3.1 stably transfected HEK-293 cells. The data are mean±standard deviation of five to seven experiments.

FIG. 4 illustrates the inhibition of $^{125}$I-dendrotoxin binding by Kv1.2-BA antibody. HEK-293 cells with stably transfected Kv1.2 channels were incubated with $^{125}$I-labeled α-dendrotoxin (10 nM; 290 Ci/mmol) in the presence of the indicated concentrations of Kv1.2-BA antibody. Preimmune IgG did not have significant effects. At 500 nM, preimmune IgG produced about 10% inhibition of $^{125}$I-dendrotoxin binding. Data are expressed as fractions of dendrotoxin binding compared with controls in which no Kv1.2-BA antibody was added. Data are representative of three similar experiments.

FIG. 5A shows whole-cell potassium currents from NG108-15 cells in the absence (NG108-15 cells) or presence (+Kv1.2-BA) of the blocking antibody Kv1.2-BA. Kv1.2-BA (250 nM) reduced the whole-cell K$^+$ currents by about 75%. FIG. 5B shows that the control antibody Kv1-NA (250 nM) reduced the current by about 25%. Data are representative of six similar experiments.

FIG. 6A illustrates Kv3.1 currents in Kv3.1 stably transfected HEK-293 cells in the absence (HEK/Kv3.1) or presence (+Kv3.1-BA) of Kv3.1-BA. Addition of 250 nM of Kv3.1-BA led to an about 80% suppression of Kv3.1 currents. FIG. 6B illustrates that Kv3.1-BA blockage is concentration dependent. Data points were taken at 15 minutes after the addition of antibody. FIGS. 6C and 6D show that Kv3.1-BA has limited effects on Kv1.2 currents in Kv1.2 stably transfected HEK-293 cells. The data are mean±SD of five to seven experiments.

DETAILED DESCRIPTION OF THE INVENTION

The present invention relates to a method of designing an ion channel blocker for an ion channel which includes providing an ion channel having an external vestibule portion and providing an antibody, binding portion, probe, or ligand specific to the external vestibule portion of the ion channel, where the antibody, binding portion, probe, or ligand inhibits ion transport through the ion channel.

Another aspect of the present invention relates to a method of inhibiting the ion transport through an ion channel having an external vestibule portion which includes providing an ion channel blocker which is specific to the external vestibule portion of the ion channel under conditions effective to inhibit ion transport through the ion channel.

Yet another aspect of the present invention relates to a method of screening a drug for effectiveness as an ion channel blocker for an ion channel where the ion channel has an external vestibule portion. The method includes contacting a cell having an ion channel with an ion channel blocker candidate and evaluating the cell to determine if the ion channel blocker candidate binds to the external vestibule portion of the ion channel and inhibits ion transport through the ion channel.

Yet another aspect of the present invention relates to an antibody where the antibody, binding portion, probe, or ligand which inhibits ion transport of an ion channel by binding to an external vestibule portion of the ion channel.

Ion channels are generally discussed in Jan, L. Y., et al., *Annu. Rev. Neurosci.*, 20:91–123 (1997) and Jan, L. Y., et al., *Annu. Rev. Physiol.*, 54:537–555 (1992), which are hereby incorporated by reference.

The ion channel blockers obtained in accordance of the present invention are any compounds which will bind to the ion channel to inhibit ion transport through the ion channel. Preferably, the ion channel blockers bind to an external vestibule portion of the ion channel. The ion channel blockers may be antibodies, binding portions thereof, probes, or ligands. Typically, the ion channel blockers are antibodies.

Figure 1A:
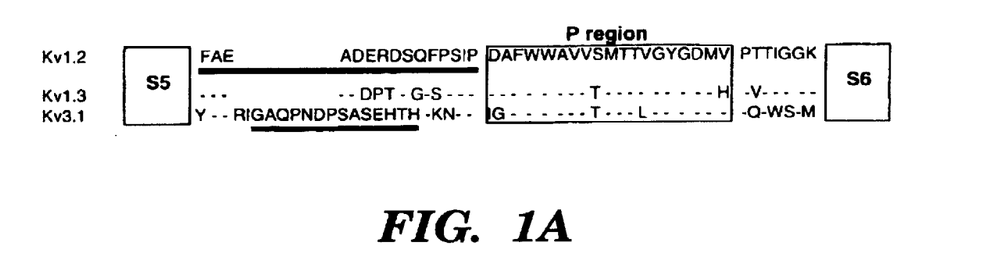
FIGS. 1A–1E show the S5–S6 linker region of Kv1.2, Kv1.3 and Kv3.1 potassium channels.

Ion transport to be inhibited according to the present invention include ion transport through potassium, sodium, calcium, and chloride channels. Preferably, the portion of the ion channel to be blocked is the external vestibule portion. Most preferably, the external vestibule portion is located between the S5 transmembrane and the pore forming region of the channel protein or between the pore forming region and the S6 transmembrane of the channel protein (FIG. 1A). For example, the external vestibule portion is a 15 amino acid peptide from Kv1.2 potassium channel having SEQ. ID. NO. 1:

```
Phe Ala Glu Ala Asp Glu Arg Asp Ser Gln Phe Pro Ser Ile Pro
 1               5                  10                  15
``` or a 14 amino acid peptide from Kv3.1 potassium channel having SEQ. ID. NO. 3:

```
Gly Ala Gln Pro Asn Asp Pro Ser Ala Ser Glu His Thr His
 1               5                  10
``` or a 15 amino acid peptide from Kv1.3 potassium channel having SEQ. ID. NO. 4:

```
Phe Ala Glu Ala Asp Asp Pro Thr Ser Gly Phe Ser Ser Ile Pro
 1               5                  10                  15
``` or any other Kv related channels(Jan, L. Y. et al., *Annu. Rev. Physiol.* 54:537–555(1992), which is hereby incorporated by reference).

The term "inhibit" or "inhibiting" as used in the present application refers to the ability of the ion channel blocker of the present invention to prevent passage of (i.e. block) the ions through the ion channel. Although not meaning to be bound be theory, it is believed that the channel blocker of the present invention binds to the target peptide sequence and physically blocks the permeation of ions through the pore. Alternatively, ion channel blocker binding could cause a conformational change in the channel protein that closes the pore.

Preferably, the channel is contained in a mammalian cell, such as a neuronal cell, a cardiac myocyte, a muscle cell, or any other excitable cell.

As indicated above, ion channel blockers which bind to the external vestibule portion of an ion channel are utilized. These ion channel blockers include antibodies, such as monoclonal and polyclonal antibodies, antibody fragments, half-antibodies, hybrid derivatives, probes, or other molecular constructs.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature*, 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.*, 6:511 (1976), which is hereby incorporated by reference.) This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow et. al., editors, *Antibodies: A Laboratory Manual* (1988), which is hereby incorporated by reference.

In addition to utilizing whole antibodies, binding portions of such antibodies can be used. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, New York: Academic Press, pp. 98–118 (1983), which is hereby incorporated by reference.

The present invention also relates to probes found either in nature or prepared synthetically by recombinant DNA procedures or other biological procedures. Suitable probes are molecules which bind to the external vestibule portion of the ion channels identified by the antibodies of the present invention. Such probes can be, for example, proteins, peptides, lectins, or nucleic acid probes.

The external vestibule portions of the ion channels listed herein include sequences which are substantially the same as the sequences listed herein. Variations, may be made by, for example, the deletion or addition of amino acids that have minimal influence on the properties, structure, or nature of the amino acid. Amino acid additions, deletions, and/or substitutions which do not negate the ability of the resulting protein to raise an antibody capable of blocking an external vestibule portion of an ion channel are within the scope of an amino acid sequence corresponding to or having or as shown in a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. As used herein, two amino acid residues are conservative substitutions of one another where the two residues are of the same type. In this regard, for purposes of the present invention, proline, alanine, glycine, serine, and threonine, all of which are neutral, weakly hydrophobic residues, are of the same type. Glutamic acid and aspartic acid, which are acidic, hydrophilic residues, are of the same type. Another type of residue is the basic, hydrophilic amino acid residues, which include histidine, lysine, and arginine. Leucine, isoleucine, valine, and methionine all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French et al., *J. Molecular Evolution* 19:171–175 (1983), Taylor, *J. Theor. Biol.* 119:205–218 (1986), and Bordo et al., *J. Mol. Biol.* 217:721–729 (1991).

Any one of a number of methods well known in the art can be used to identify a hybridoma cell which produces an antibody with the desired characteristics. These include screening the hybridomas with an ELISA assay, Western blot analysis, or radioimmunoassay (Lutz et al., *Exp. Cell. Res.* 175:109–124 (1988), which is hereby incorporated by reference).

Hybridomas secreting the desired antibodies are cloned and the class and subclass are determined using procedures known in the art.

Having described the ion channel blocker of the present invention, and methods for designing the ion channel blocker, this ion channel blocker can be used in a method of screening a drug for effectiveness as an ion channel blocker. The ion channel blocker which is specific to the external vestibule portion of the ion channel is contacted with a cell which contains ion channels. The cell is then evaluated to determine whether the ion channel blocker inhibits ion transport through the ion channel. From this evaluation, ion channel blockers which inhibit ion transport through the ion channel can be found. The ability of the ion channel blocker to inhibit ion transport through the ion channel can be assayed according to methods known in the art, such as voltage clamp analysis of the channel as described in Huang et al., *Cell* 75:1145–1150 (1993), which is hereby incorporated by reference.

Thus, the present invention may screen drugs useful in treating diseased states, such as hypertension, cardiac ischemia, cerebral ischemia, bronchi construction, and neurological diseases.

EXAMPLES

Materials and Methods

Affinity-purified polyclonal antibodies and immunoblot. Kv1.2-BA, Kv1-NA, and Kv3.1-BA rabbit polyclonal antibodies were made and affinity purified through Genemed Biotechnologies, Inc. (South San Francisco, Calif.). A cysteine residue was added to the carboxyl end of the peptide having SEQ. ID. No. 1:

```
Phe Ala Glu Ala Asp Glu Arg Asp Ser Gln Phe Pro Ser Ile Pro
1               5                   10                  15
``` or the amino end of the peptide having SEQ. ID. No. 2:

```
Asp Pro Leu Arg Asn Glu Tyr Phe Phe Asp Arg Asn Arg Pro Ser
1               5                   10                  15
``` or the carboxyl end of the peptide having SEQ. ID. No. 3:

```
Gly Ala Gln Pro Asn Asp Pro Ser Ala Ser Glu His Thr His
1               5                   10
``` for keyhold limpet hemocyanin conjugation. Rabbit antiserum was purified with the peptide-affinity matrix. The specificity of these antibodies was confirmed by competition experiments with different peptides during immunoblotting. Immunoblot of membrane proteins (30 µg per lane) from HEK and transfected HEK cells was done as described, with some modifications (Langhans-Rajasekaran, S. A. et al., *Proc. Natl. Acad. Sci. USA* 92:8601–8605 (1995); Wan Y. et al., *Nature,* 380:541–544 (1996), which are hereby incorporated by reference). Boiling lysis solution (1% Triton X-100, 150 mM NaCl, 10 mM Tris, pH 7.4, 1 mM EDTA, 1 mM EGTA, 0.5% NP-40, 0.1% SDS, 1% Na-deoxycholate) was used to resuspend membrane proteins.

Electrophysiological recordings with HEK-293 cells. Maintenance, growth, and stable transfection of HEK-293 cells were performed as described (Huang, X. Y. et al., *Cell* 75:1145–1156 (1993); Langhans-Rajasekaran, S. A. et al., *Proc. Natl. Acad. Sci. USA* 92:8601–8605 (1995), which are hereby incorporated by reference). At each passage, some cells were plated onto 2.5-cm culture dishes with small cover slips for electrophysiological measurements. Electrophysiological recordings were made on the same day. Whole-cell patch-clamp recordings were performed as described, with some modifications (Huang, X. Y. et al., *Cell* 75:1145–1156 (1993), which is hereby incorporated by reference). Recordings were done at room temperature with pipettes pulled from micro-hematocrit capillary tubes with resistances of 2 to 4 MΩ. The pipette solution contained 180 mM K-Asp, 5 mM NaCl, 5 mM Na-HEPES, 5 mM EGTA, 0.28 mM CaCl$_2$, 0.8 mM MgCl$_2$, 1.5 mM ATP, 0.1 mM GTP, pH adjusted to 6.7 with HCl. The bath solution contained 118 mM NaCl, 2.5 mM KCl, 1.8 mM CaCl$_2$, 0.8 mM MgCl$_2$, 5 mM Na-HEPES, 23 mM Glucose, 54 mM Sucrose, pH adjusted to 7.4 with NaOH. Whole-cell currents were elicited by voltage pulses of 300 ms duration from a holding potential of −70 mV. Current was measured in the range from −40 mV to 60 mV, varying the voltage in 10-mV steps. Series resistance values after seal formation were less than 3 MΩ and were electronically compensated. The current signals were low pass filtered at 5 kHz and leak subtracted. The data were collected by using Axopatch 200A via pCLAMP6 (Axon, Forster City, Calif.) To investigate the effects of antibodies on membrane potassium currents, cells were patched for 5 minutes to obtain a stable baseline before antibodies were added to the recording chamber.

Electrophysiological recordings with Neuronal cells. Maintenance and growth of the neuronal NG108-15 cells are as described (Huang, X. Y. et al., *Cell* 75:1145–1156 (1993); Han, H. Q. et al., *Nature,* 349:697–700 (1991), which are hereby incorporated by reference). At each passage, some cells were plated onto 2.5-cm collagen-coated culture dishes with small cover slips for electrophysiological measurements. Electrophysiological recordings were made about 3 to 7 days after differentiation. Whole-cell patch-clamp recordings of potassium currents were performed as described (Wilk-Blaszczak, M. A. et al., *Neuron,* 13:1215–1224 (1994), which is hereby incorporated by reference). Recordings were done at room temperature using a 2 to 4 MΩ resistance electrode. The pipette solution contained 115 mM KCl, 0.1 mM MgCl$_2$, 40 mM HEPES, 3 mM ATP, 0.1 mM GTP, pH adjusted to 7.3 with KOH. The bath solution contained 125 mM NaCl, 5.4 mM KCl, 1.8 mM CaCl$_2$, 1 mM MgCl$_2$, 20 mM HEPES, 5 mM Glucose, pH adjusted to 7.4 with NaOH. Recording protocol, data collection, and analysis were done as described above for HEK-293 cells.

Dendrotoxin Binding Assay. Binding assay was performed as previously described for agonist binding to muscarinic receptors (Wan et al., *J. Biol. Chem.* 272:17209–17215 (1997), Wan et al., *Nature* 380:541–544 (1996); and Bence et al., *Nature* 389:296–299 (1997), which are hereby incorporated by reference). Briefly, HEK293 cells stably expressing Kv1.2 channel proteins were grown in 12-well dishes. After being washed two times with Hank's balanced salt solution ("HBSS") plus 10 mM HEPES (pH 7.4), 300 µl binding solution was added to each well. The binding solution contains HBSS plus 10 mM HEPES (pH 7.4), 1 mg/ml BSA, 1 mg/ml bacitracin, 1 mM PMSF, 10 nM $^{125}$I-α-dendrotoxin (290 Ci/mmol) (Amersliam Corp., Arlington Heights, Ill.; or Alomone Labs, Jerusalem, Israel), and various concentrations of Kv1.2-BA antibody. After incubation for 4 hours at 4° C., cells were washed two times with HBSS plus 10 mM HEPES (pH 7.4) to remove unbound $^{125}$I-dendrotoxin. Cells were then lysed with 1 ml of 0.4 N NaOH and transferred to borosilicate tubes. The bound $^{125}$I-dendrotoxin was counted with a gamma counter. Nonspecific binding of $^{125}$I-dendrotoxin to cells was determined in the presence of excess (10 µM) unlabeled dendrotoxin. Nonspecific inhibition of antibody on dendrotoxin binding was examined in the presence of 500 nM of pre-immune IgG with <10% inhibition.

Data Analysis Data for multisite inhibition can be expressed in terms of a Hill equation (Segel, I. H. *Enzyme Kinetics*, John Wiley & Sons, Inc., New York, (1993), which is hereby incorporated by reference):

$$\log \{I/I_0/(1-I/I_0)\} = -n\log [\text{antibody}] + \log K'$$

where $I_0$ is the current amplitude before the addition of the antibody; I is that after the addition of the antibody;

[antibody] is the concentration of the antibody; and n indicates the number of binding sites of the antibody on the channel. $IC_{50}$ is related to K' as $IC_{50}$ n=K'. A Hill plot for the inhibition by both Kv1.2-BA or Kv3.1-BA antibodies gave the slope of the Hill plot –0.75, indicating only one antibody binding to one channel complex. Thus, the Hill equation can be simplified as:

$$I/I_0=1/(1+[antibody]/K').$$

All curve fittings were performed using this equation.

Example 1

Suppression of Kv1.2 Current by Kv1.2-BA Antibody

Figure 1B:
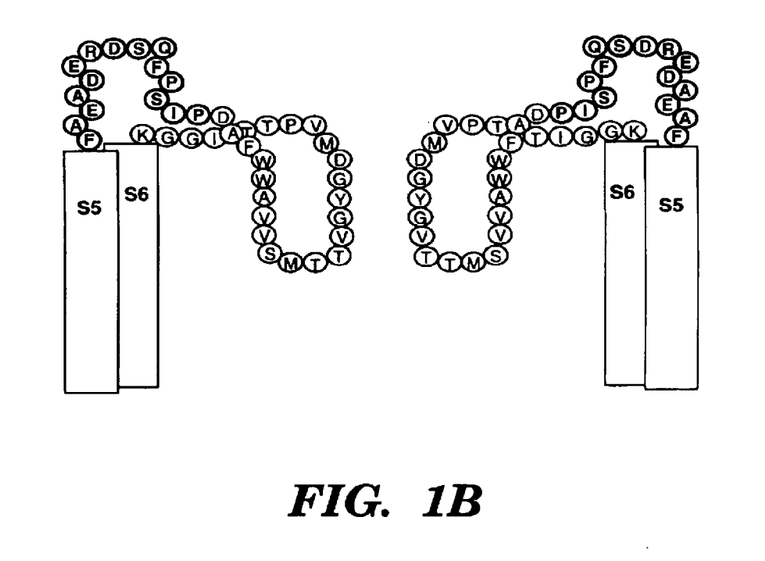
Figure 1C:
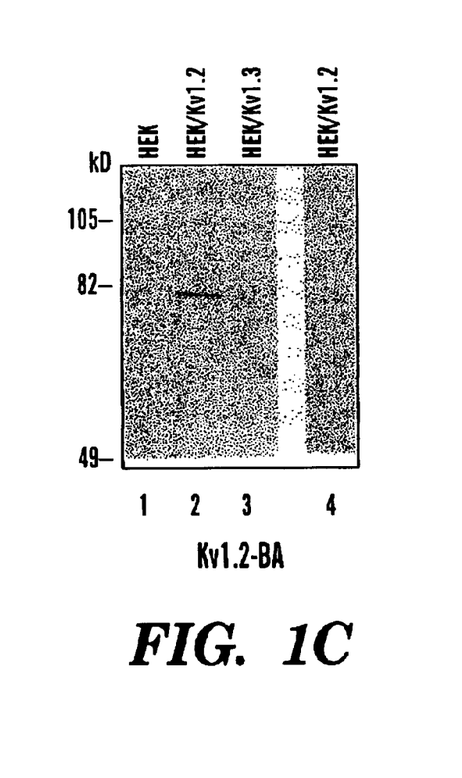
Figure 2A:
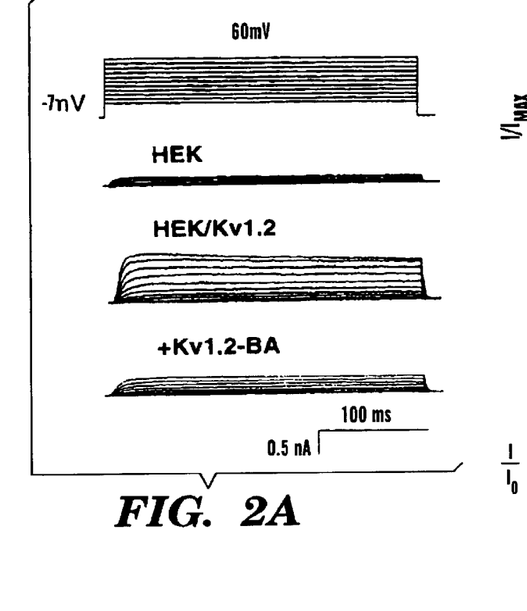
FIGS. 2A–2E show the blockage of Kv1.2 currents by Kv1.2-BA antibody.
Figure 2B:
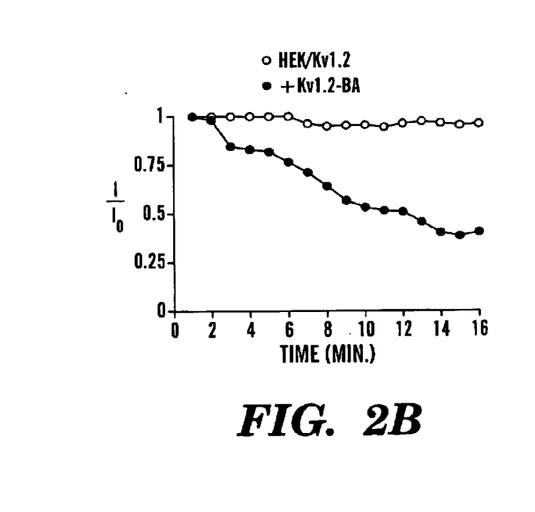
Figure 2C:
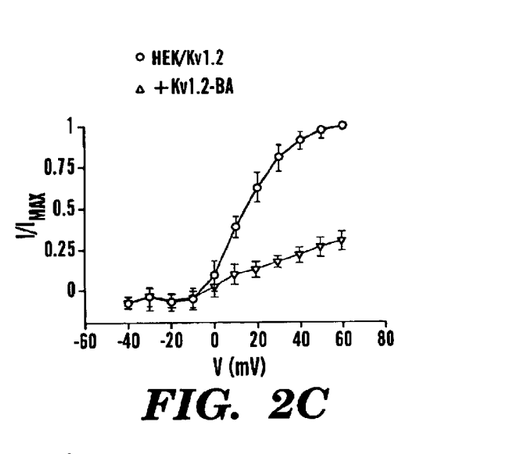
Figure 2D:
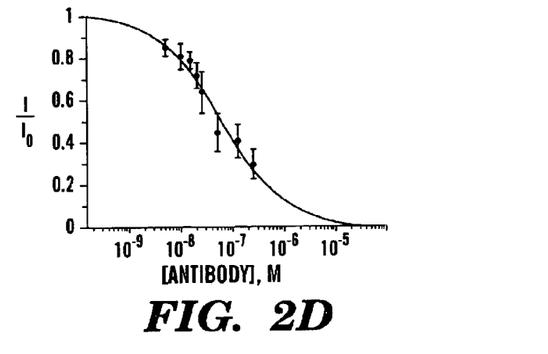

To test whether antibodies specific for peptides around the pore-regions of individual ion channels can be used as a channel blocker, the blocking ability of an affinity-purified polyclonal antibody generated against a 15 amino-acid peptide of a delayed-rectifier potassium channel Kv1.2 (Huang, X. Y. et al., *Cell* 75:1145–1156 (1993)) (FIG. 1A) was examined. This sequence identified as SEQ. ID. NO. 1:

Phe Ala Glu Ala Asp Glu Arg Asp Ser Gln Phe Pro Ser Ile Pro
1           5                   10                  15 located between the S5 transmembrane and the pore-forming (P) region, is very likely part of the external vestibule (or the outer mouth) of the channel protein (FIG. 1B) (Lu, Q. et al., *Science* 268:304–307 (1995); Hidalgo, P. et al., *Science* 268:307–310 (1995); Aiyar, J. et al., *Neuron* 15:1169–1181 (1995), which are hereby incorporated by reference). Kv1.2 was stably expressed in a mammalian cell line, HEK-293 cells (Huang, X. Y. et al., *Cell* 75:1145–1156 (1993), which is hereby incorporated by reference). The affinity-purified polyclonal antibody (Kv1.2-BA) detected Kv 1.2 protein in plasma membranes of Kv1.2-transfected cells (FIG. 1C). Whole-cell patch-clamp recording revealed large outward potassium currents, elicited at depolarizing voltages, that are absent in untransfected HEK-293 cells (FIG. 2A). Addition of 250 nM of the affinity-purified polyclonal antibody (Kv1.2-BA) to the external solution blocked about 70% of the Kv1.2 currents (FIG. 2). The current amplitude decline, seen only after addition of Kv1.2-BA, occurred within 1 minute and reached about 70% suppression in about 7–15 minutes (FIG. 2B). The Kv1.2 current is stable in the absence of antibodies (FIG. 2B). The current is decreased by the antibody Kv1.2-BA for all voltages ≧0 mV (FIG. 2C). Also, the suppression was antibody concentration-dependent: with a rise in concentration of Kv1.2-BA, the inhibition of Kv1.2 currents increases (FIG. 2D). The data for the channel inhibition by the blocking antibody could be well fitted by an equation for 1:1 binding between the antibody and the Kv1.2 channel with an $IC_{50}$ of 54 nM (see data analysis in Materials and Methods). This $IC_{50}$ is similar to the $K_d$ of most potassium channel neurotoxins. Thus, the antibody Kv1.2-BA can suppress the Kv1.2 current in Kv1.2 transfected cells.

Example 2

Figure 2E:
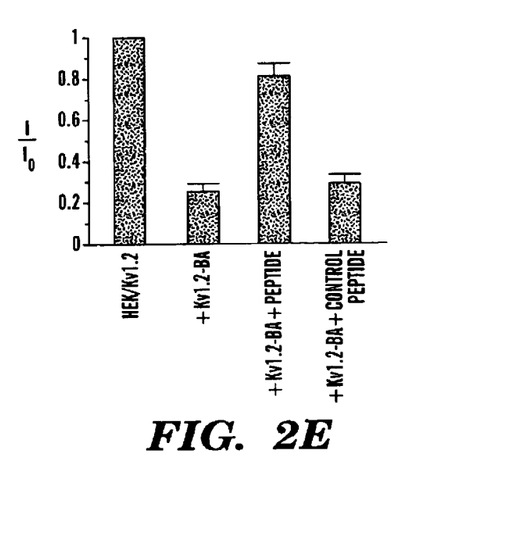

To ensure that the Kv1.2-BA antibody does indeed bind to the external region of Kv1.2 channel protein and that the blocking effect is due to the binding of the Kv1.2-BA antibody to the channel protein, Kv1.2-BA antibody was preincubated with the immunogenic peptide that was used to generate Kv1.2-BA. If blocking is due to binding of the antibody to the peptide sequence in the external vestibule of the channel protein, preincubation with the peptide should prevent the inhibition. As shown in FIG. 2E, addition of 250 nM Kv1.2-BA after preincubation with the immunogenic peptide only produced about 25% inhibition. Preincubation with a control peptide did not inhibit the Kv1.2-BA-induced suppression of Kv1.2 currents (FIG. 2E). Thus, the majority of the inhibition by Kv1.2-BA on Kv1.2 currents is due to specific finding of Kv1.2 to the particular peptide sequence around the pore region of Kv1.2 channels. The residual about 25% inhibition is likely due to either nonspecific blocking of the channel by high concentrations of proteins in the bath solution or the presence of another antiserum in the polyclonal antibody preparation that fortuitously recognize sequences of the channel protein. Nonetheless, Kv1.2-BA can significantly block Kv1.2 currents in Kv1.2-transfected cells.

Example 3

No Effect of Kv1.2 Current by a Control Antibody Kv1-NA

Figure 1D:
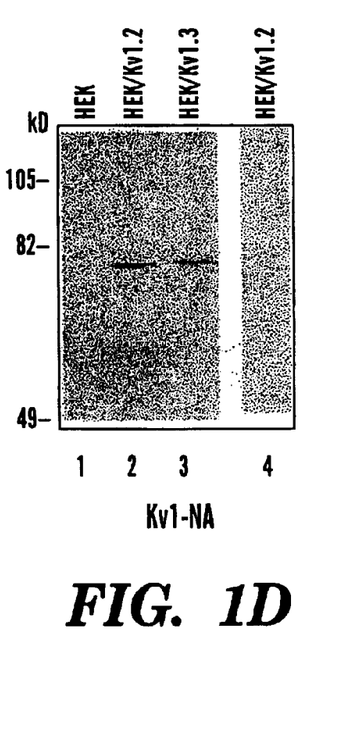
Figure 3A:
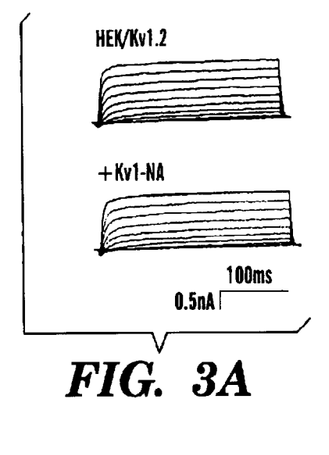
FIGS. 3A–3F illustrate a demonstration of the specificity of the blockage by Kv1.2-BA.
Figure 3B:
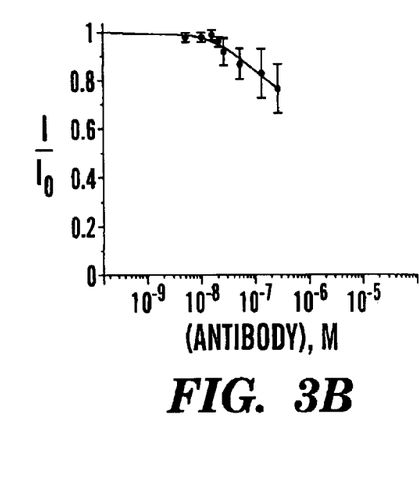

To further exclude the possibility that the Kv1.2 BA blocking effects were non-specific and that any antibody added outside cells somehow interferes the channel function, the effects on the Kv1.2 currents by another affinity-purified polyclonal antibody (Kv1-NA) was examined (FIG. 3A and 3B). Kv1-NA was generated against a peptide having SEQ ID. NO. 2:

Asp Pro Leu Arg Asn Glu Tyr Phe Phe Asp Arg Asn Arg Pro Ser
1              5                  10                    15 from the intracellular N-terminus of Kv1.2, which is identical in all members of the Kv1 family (FIG. 1D). Addition of this control antibody Kv1-NA had no effect at low concentrations (<20 nM) and very small effects at very high concentrations (>100 nM) on the Kv1.2 currents (FIG. 3B). These results indicate that the effect of antibody Kv1.2-BA is specific.

Example 4

Effects of Related Kv1.3 or Kv3.1 Currents by Kv1.2-BA Antibody

Figure 3C:
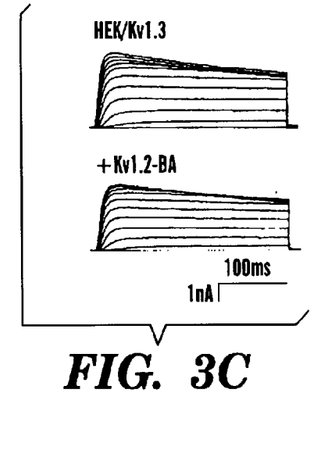
Figure 3D:
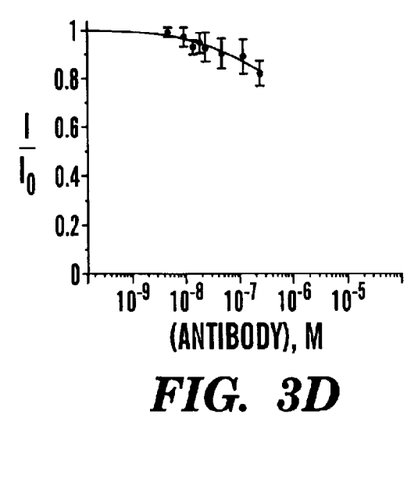
Figure 3E:
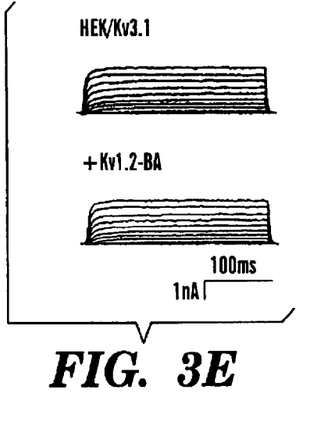
Figure 3F:
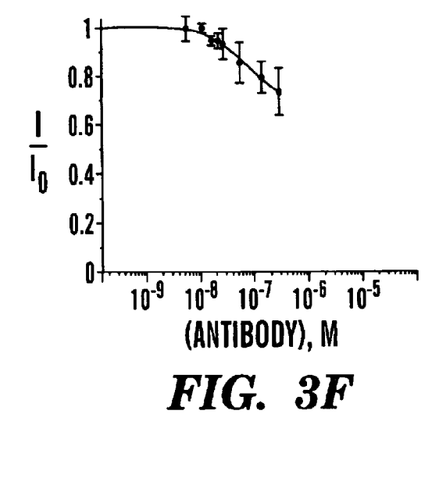

To additionally ensure the specificity, the Kv1.2-BA antibody was tested on related potassium channels. Kv1.3 belongs to the same subfamily of delayed-rectifier potassium channels as Kv1.2. Kv1.3 has the same sequence around the pore-region as Kv1.2, with the exception of five amino acids (FIG. 1A). When stably expressed in HEK-293 cells, Kv1.3 exhibits C-type slow inactivation (Attali, B. *J. Biol. Chem.* 267:8650–8657 (1992); Panyi, G. et al. *Biophys. J.* 68:896–903 (1995), which are hereby incorporated reference) (FIG. 3C). In contrast to the results obtained with Kv1.2 currents, addition of Kv1.2-BA had little effects on Kv1.3 currents, only small effect at high concentrations (similar to the residual effect of Kv1.2 currents by Kv1.2-BA preincubated with the immunogenic peptide) (FIGS. 3C and 3D). Kv3.1 is another delayed-rectifier $K^+$ channel, but belongs to a different subfamily (Yokoyama, S. et al. *FEBS Letters* 259:37–42 (1989); Luneau, C. J. et al. *Proc. Natl. Acad. Sci. USA* 88:3932–3936 (1991), which are hereby incorporated by reference). Although Kv3.1 has high sequence homology with Kv1.2 in transmembrane domains and pore-forming regions, it differs from Kv1.2 in the region where Kv1.2-BA binds (FIG. 1A). As would be expected, there was only a small change of Kv3.1 currents expressed in HEK-293 cells after addition of Kv1.2-BA (FIGS. 3E and 3F). These experiments demonstrated that Kv1.2-BA specifically blocks the Kv1.2 currents, without affecting other related $K^+$ currents.

Example 5

Inhibition of Binding of $^{125}$I-Dendrotoxin by Kv1.2-BA

Figure 4:
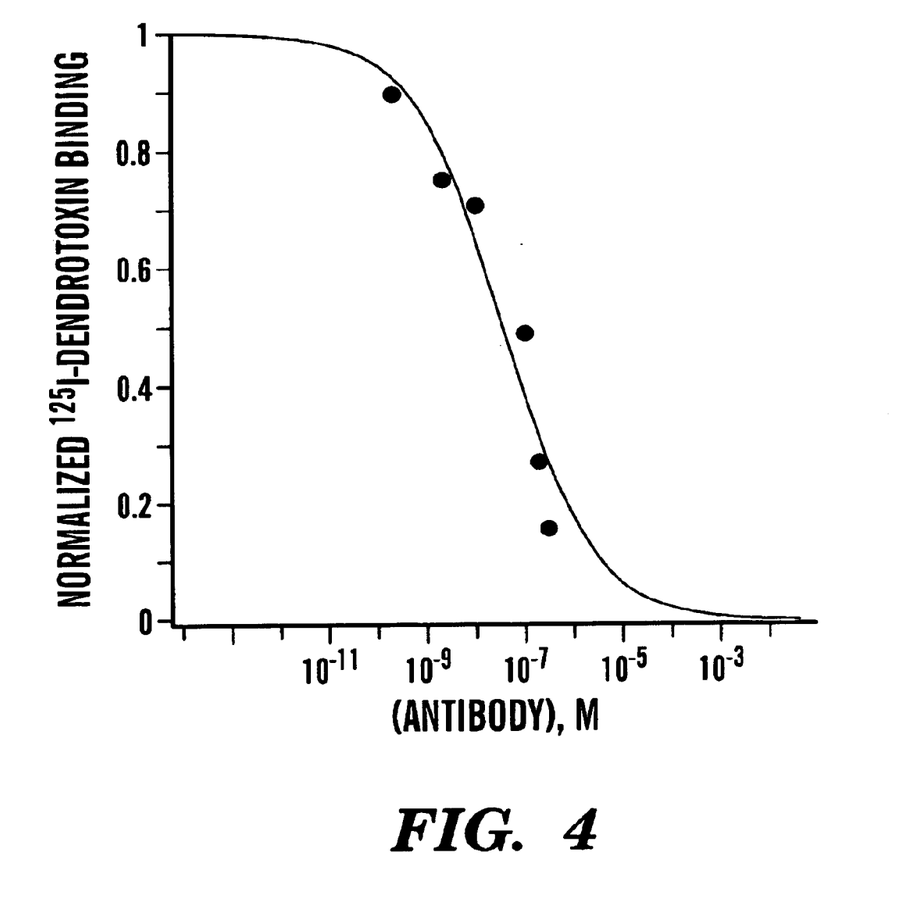

Kv1.2 channel protein is one of the major receptors for dendrotoxin in vivo (Scott, *J. Biol. Chem.* 265:20094–20097 (1990)), which is hereby incorporated by reference). Since α-dendrotoxin also binds to the external vestibule of Kv1.2 channel protein (Hurst, R. S. *Mol. Pharmacol.* 40:572–576 (1991), which is hereby incorporated by reference), it is expected that binding by α-dendrotoxin and Kv1.2-BA antibody should be mutually exclusive. If the Kv1.2 channel protein is first bound with the Kv1.2-BA antibody, then binding of α-dendrotoxin to Kv1.2-BA channel protein should be decreased compared to the binding in the absence of Kv1.2-BA antibody due to the occupancy of the channel proteins by the antibody that excludes the binding of α-dendrotoxin. As shown in FIG. 4, increased concentrations of Kv1.2-BA led to the inhibition of $^{125}$I-α-dendrotoxin binding in Kv1.2-transfected HEK cells. Thus, this data further demonstrates that Kv1.2-BA blocks Kv1.2 currents by binding to the external vestibule of Kv1.2 channel protein.

Example 6

Suppression of Endogenous Kv1.2 Current by Kv1.2-BA Antibody

Figure 5A:
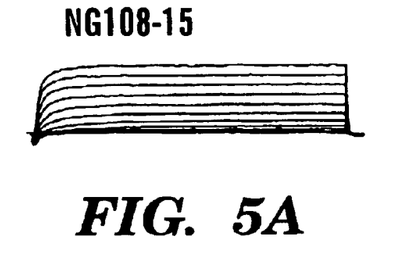
FIGS. 5A and 5B show the blockage of endogenous Kv1.2 currents by Kv1.2-BA in neuronal cells.
Figure 5B:
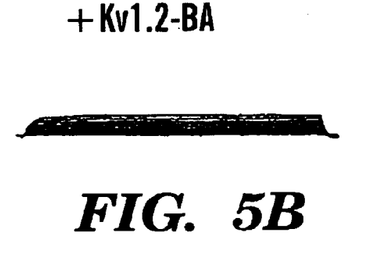
Figure 5C:
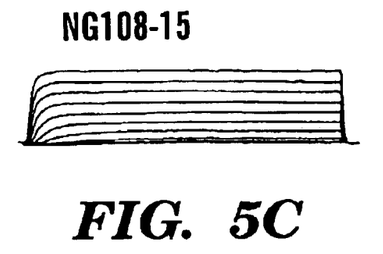
Figure 5D:
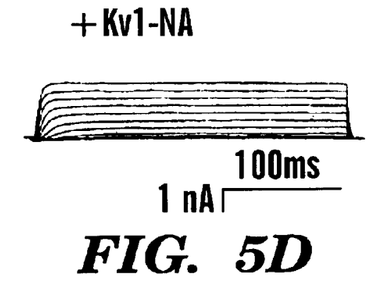

The method of the present invention was tested in a neuronal cell line. Previously, Kv1.2 had also been cloned by screening a cDNA library made from the neuronal NG108-15 cells, and it has been shown that Kv1.2 is abundantly expressed in NG108-15 cells (Yokoyama, S. et al. *FEBS Letters* 259:37–42 (1989), which is hereby incorporated by reference). Therefore, whole-cell patch-clamp analysis was performed on NG108-15 cells (Han. H. Q. et al. *Nature* 349:697–700 (1991); Wilk-Blaszcak, M. A. et al., *Neuron* 13:1215–1224 (1994), which are hereby incorporated by reference) (FIG. 5). Addition of the blocking antibody Kv1.2-BA (250 nM) resulted in a 76±12% (n=6) decrease of the whole-cell potassium currents within 10–15 minutes, a significantly (P<0.002, paired t test) higher inhibition than that caused by the control antibody Kv1-NA (25±8%[n=6]) decrease over the same period with 250 nM Kv1-NA). Untreated cells showed a 8±3%(n=6) decrease. These results demonstrate that the Kv1.2-BA antibody blocks endogenous Kv1.2 current as well as heterologously expressed Kv1.2 currents.

Example 7

Application of the Method to Another Subfamily of $K^+$ Channels

Figure 1E:
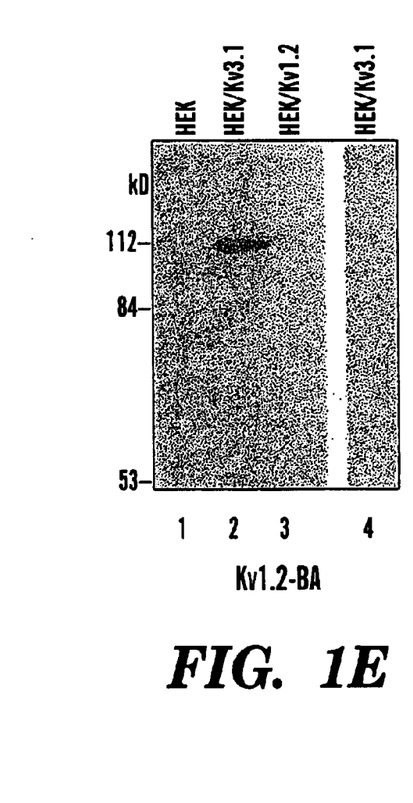
Figure 6A:
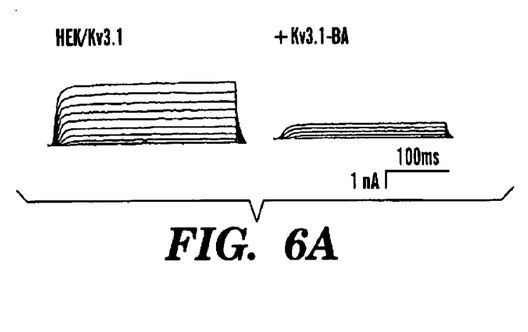
FIGS. 6A–6D shows the blockage of Kv3.1 currents by Kv3.1-BA antibody.
Figure 6B:
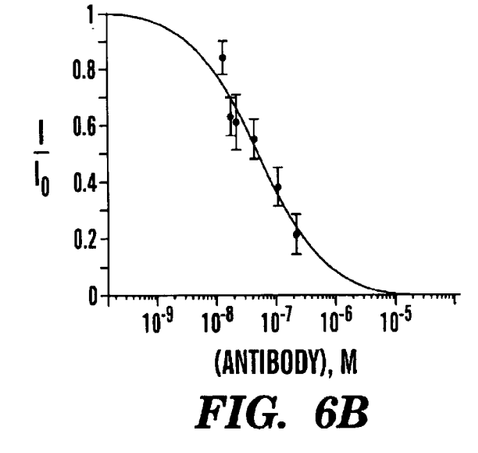
Figure 6C:
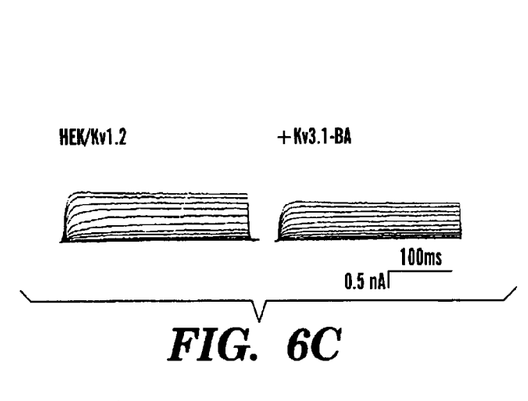
Figure 6D:
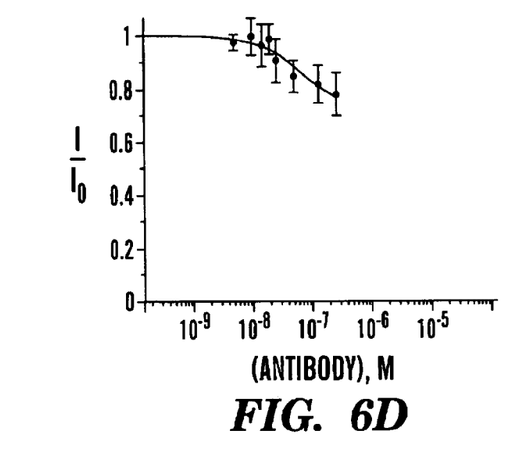

To extend the method of the present invention to other subfamilies of $K^+$ channels, another polyclonal antibody was generated against a 14 amino-acid peptide, having SEQ. ID. No. 3:

```
Gly Ala Gln Pro Asn Asp Pro Ser Ala Ser Glu His Thr His
 1                   5                  10
``` from the external vestibule of the Kv3.1 channel protein (FIG. 1A and 1E). This affinity-purified anti-Kv3.1 antibody (Kv3.1-BA) detected Kv3.1 protein in plasma membranes of Kv3.1-transfected HEK-293 cells (FIG. 1E). Kv3.1-BA at 250 nM blocked about 79% of the Kv3.11 currents from Kv3.1-transfected HEK cells (FIG. 6A). The Kv3.1 current is stable in the absence of antibodies. The suppression is antibody dose dependent (FIG. 6B). The $IC_{50}$ is 58 nM. This Kv3.1-BA antibody had limited effects on Kv1.2 currents (FIGS. 6C and 6D). Thus, the antibody Kv3.1-BA can specifically suppress Kv3.1 currents.

Discussion

In practice, like any other methods using antibodies, the concentration used is important and controls are essential. It is useful to test several concentrations of antibodies to obtain appropriate amounts to maximize inhibition and minimize nonspecific background suppression. If the antibody is used at too high a concentration, high background (nonspecific suppression) can result. If the antibody concentration is too low, the inhibition will be too small to be certain of specificity. In general, the optimal concentrations for purified polyclonal antibodies will be in the range of about 20–60 nM. At concentrations <60 nM, the specific antibodies could reduce the currents significantly (as high as 50%), while nonspecific antibodies produced no suppression other than rundown (<10%). When examining endogenous currents, it is very important to compare the suppression produced by the channel-blocking antibody with a control antibody, or one can perform the experiments in the presence and absence of the immunogenic peptide used to generate the antibody and compare the differences.

Given the remarkable specificity and selectivity of antibodies for their targets, the method of the present invention provides a superior approach to rationally design specific ion channel blockers. A large number of $K^+$ channels expressing similar properties makes it a difficult task to identify a native $K^+$ current as one expressed by a cloned $K^+$ channel gene. At present time, the identification of a particular current in cells possessing a broad array of overlapping currents depends on a limited array of pharmacological tools. Although the availability of mutants is of great help for such an endeavor, there are not many $K^+$ channel mutants identified in vertebrates. Approaches targeted at the biosynthesis or assembly of channel proteins such as introducing antisense oligonucleotides or expressing dominant negative mutant channels in native cells have limitations, for example, the dependence on the turnover rate of endogenous channel proteins (Tu, L. et al. (1995) *Biophys. J.* 68:147–156; Chung, S. et al. (1995) *Proc. Natl. Acad. Sci USA* 92:5955–5959). Since the method of the present invention is aimed at the functional membrane channel proteins, it avoids such limitation. Furthermore, antibodies have been raised that detect single amino acid substitutions, or differentiate between phosphorylated and unphosphorylated peptides (Harlow, E. *Antibodies* (Cold Spring Harbor Laboratory, 1988). Thus, they are excellent tools to discriminate among structurally related ion channels.

The biophysical mechanism of the blocking ability of Kv1.2-BA on Kv1.2 currents or Kv3.1-BA on Kv3.1 currents is not yet clear. The target peptide sequence is close to the ion flux pathway, and it is likely that the antibody binds to the peptide and physically blocks the permeation of $K^+$ ions as is the case with sorption toxins (MacKinnon, R. et al., *J. Gen. Physiol.* 91:335–349 (1988), which is hereby incorporated by reference). Alternatively, antibody binding could cause a conformational change in the channel protein that closes the pore. Regardless of the mechanism, however, the present invention is a novel approach to identify a specific ion channel involved in producing a particular endogenous current. This immuno-electrophysiological approach should also be applicable to other ion channels. Also, this method can be used or modified as a rational drug design using ion channels as therapeutic targets. In addition, it should be possible to design channel openers by generating antibodies that force the channel into an open configuration. Furthermore, using the same peptide or other nearby peptides as probes, it is possible to screen for small peptides or oligonucleotides that could be used as ion channel blockers using combinatorial chemistry.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of identifying an ion channel blocker for a voltage-sensitive potassium, sodium, or calcium channel, said method comprising:

(a) providing a functional voltage-sensitive potassium, sodium, or calcium channel having an external vestibule portion, wherein said external vestibule portion is the portion of the channel located between an S5 transmembrane and pore forming region of the channel or between the pore forming region and an S6 transmembrane of the channels;

(b) identifying a compound that binds to the external vestibule portion; and (c) determining whether the compound identified in step (b) inhibits transport through the channel, thereby identifying, as an ion channel blocker for the channel, an antibody, binding portion of the antibody, probe, or ligand which inhibits ion transport through the channel by binding to the external vestibule portion of the channel.

2. The method according to claim 1, wherein the ion channel blocker is an antibody.

3. The method according to claim 2, wherein the channel is contained in a mammalian cell.

4. The method according to claim 2, wherein the channel is a Kv ion channel.

5. The method according to claim 4, wherein the antibody is a polyclonal antibody.

6. The method according to claim 5, wherein the channel is a Kv1.2, Kv1.3, or Kv3.1 ion channel.

7. The method according to claim 6, wherein the external vestibule portion has a sequence corresponding to SEQ ID NO:1, SEQ ID NO:3. or SEQ ID NO:4.

8. A method of screening a drug for effectiveness as an ion channel blocker for a voltage-sensitive potassium, sodium, or calcium channel, said method comprising:

contacting a cell, which cell has a functional ion voltage-sensitive potassium, sodium, or calcium channel having an external vestibule portion, with a drug which is an ion channel blocker candidate, wherein the external vestibule portion is a portion of the channel located between an S5 transmembrane and pore forming region of the channel or between the pore forming region and an S6 transmembrane of the channel;

evaluating the cell to determine if the ion channel blocker candidate binds to the external vestibule portion of the ion channel and inhibits ion transport through the channel; and identifying a drug which binds to the external vestibule portion of the channel and inhibits ion transport through the channel as an ion channel blocker.

9. The method according to claim 8, wherein the ion channel blocker is an antibody, binding portion of the antibody, probe, or ligand.

10. The method according to claim 9, wherein the antibody is a polyclonal antibody.

11. The method according to claim 8, wherein the channel is a mammalian ion channel.

12. The method according to claim 8, wherein the channel is a Kv ion channel.

13. The method according to claim 8, wherein the channel is a Kv1.2, a Kv1.3, or a Kv3.1 ion channel.

14. The method according to claim 13, wherein the external vestibule portion has a sequence corresponding to SEQ ID NO:1, SEQ ID NO:3, or SEQ ID NO:4.

* * * * *